United States Patent
Duelli et al.

(10) Patent No.: US 11,028,439 B2
(45) Date of Patent: Jun. 8, 2021

(54) ASSAY FOR DETECTING HEPATITIS B VIRUS (HBV)

(71) Applicant: ABBOTT MOLECULAR INC., Des Plaines, IL (US)

(72) Inventors: Dominik Duelli, Des Plaines, IL (US); Wai-Bing Mak, Des Plaines, IL (US); Brian Erickson, Des Plaines, IL (US); Amanda Goldston, Des Plaines, IL (US)

(73) Assignee: ABBOTT MOLECULAR INC., Des Plaines, IL (US)

( * ) Notice: Subject to any disclaimer, the term of this patent is extended or adjusted under 35 U.S.C. 154(b) by 294 days.

(21) Appl. No.: 16/143,904

(22) Filed: Sep. 27, 2018

(65) Prior Publication Data
US 2019/0153537 A1    May 23, 2019

Related U.S. Application Data

(60) Provisional application No. 62/564,008, filed on Sep. 27, 2017.

(51) Int. Cl.
*C12Q 1/6876* (2018.01)
*C12Q 1/70* (2006.01)
*C12Q 1/6806* (2018.01)
*C12Q 1/686* (2018.01)

(52) U.S. Cl.
CPC ........... *C12Q 1/6876* (2013.01); *C12Q 1/686* (2013.01); *C12Q 1/6806* (2013.01); *C12Q 1/706* (2013.01); *C12Q 2600/112* (2013.01); *C12Q 2600/16* (2013.01); *C12Q 2600/166* (2013.01)

(58) Field of Classification Search
CPC . C12Q 1/6876; C12Q 1/706; C12Q 2600/112
See application file for complete search history.

(56) References Cited

U.S. PATENT DOCUMENTS

| | | | |
|---|---|---|---|
| 5,270,184 A | 12/1993 | Walker et al. | |
| 5,455,166 A | 10/1995 | Walker | |
| 7,015,317 B2 * | 3/2006 | Mullen | C12Q 1/706 435/29 |
| 9,085,808 B2 * | 7/2015 | Ho | C12Q 1/705 |
| 2006/0194217 A1 * | 8/2006 | Zoulim | C12Q 1/706 435/6.12 |

FOREIGN PATENT DOCUMENTS

WO     WO 2017011565 A1    1/2017

OTHER PUBLICATIONS

Yip, Use of Dual TaqMan Probes to Increase the Sensitivity of 1-Step Quantitative Reverse Transcription-PCR: Application to the Detection of SARS Coronavirus, Clin. Chem., 51(10): 1885-1888, 2005. (Year: 2005).*
GenBank Accession No. MG725248.1, Hepatitis B virus isolate NHB17003, complete genome, Jan. 24, 2018. (Year: 2018).*
Abbott RealTime HBV (FDA) Package Insert No. 51-608234/R4, Jun. 2016.
Aptima HBV Quant Assay (Hologic) Package Insert No. AW-13182-001 Rev. 001 (CE), 2018.
Chen et al., "B/C genotyping of hepatitis B virus based on dual-probe electrochemical biosensor." Journal of Electroanalytical Chemistry Jan. 2017, 785: pp. 75-79.
Geng et al., "Dual-probe assay for detection of lamivudine-resistance hepatitis B virus by real-time PCR." J Virol Methods. Mar. 2006; 132(1-2):25-31.
Gentile et al., "Vertical transmission of hepatitis B virus: challenges and solutions" Int J Womens Health, Jun. 10, 2014, 6: 605-11.
Liang, "Hepatitis B: the virus and disease" Hepatology, May 2009, 49(5): S13-21.
Lok et al., "Chronic hepatitis B" Hepatology, Dec. 2001, 34(6): 1225-41.
Schweitzer et al., "Estimations of worldwide prevalence of chronic hepatitis B virus infection: a systematic review of data published between 1965 and 2013" Lancet, Oct. 17, 2015, 386(10003): 1546-1555.
Srivastava et al., "Need for immunization against hepatotropic viruses in children with chronic liver disease" J Pediatr Gastroenterol Nutr., Sep. 2014, 59(3):393-7.
Terrault et al., "AASLD guidelines for treatment of chronic hepatitis B" Hepatology, Jan. 2016, 63(1): 261-282 (2015).
Hepatitis B Fact Sheet. [Online] Jul. 18, 2019 World Health Organization: Media Centre [retrieved on Nov. 12, 2019]. Retrieved from the Internet: <URL: www.who.int/mediaventre/factsheets/fs204/en/>.
Yeung et al., "Current issues in the management of paediatric viral hepatitis" Liver Int, Jan. 2010, 30(1): 5-18.

* cited by examiner

Primary Examiner — Angela M. Bertagna
Assistant Examiner — Carolyn L Greene
(74) Attorney, Agent, or Firm — Casimir Jones, S.C.; Melissa E. Karabinis

(57) ABSTRACT

The disclosure is directed to methods, kits, and compositions, for amplifying and detecting a human hepatitis B virus (HBV) in a sample, which comprises a variety of combinations of forward oligonucleotide primers, reverse oligonucleotide primers, and oligonucleotide probes.

9 Claims, 8 Drawing Sheets

Specification includes a Sequence Listing.

Least-Squares Regression Plot and Summary for Panel Members within the Linear Range in Plasma Least-Squares Regression Plot and Summary for Panel Members within the Linear Range in Serum Least-Squares Regression Plot for Panel Members within the Linear Range Least-Squares Regression Plot for Panel Members within the Linear Range

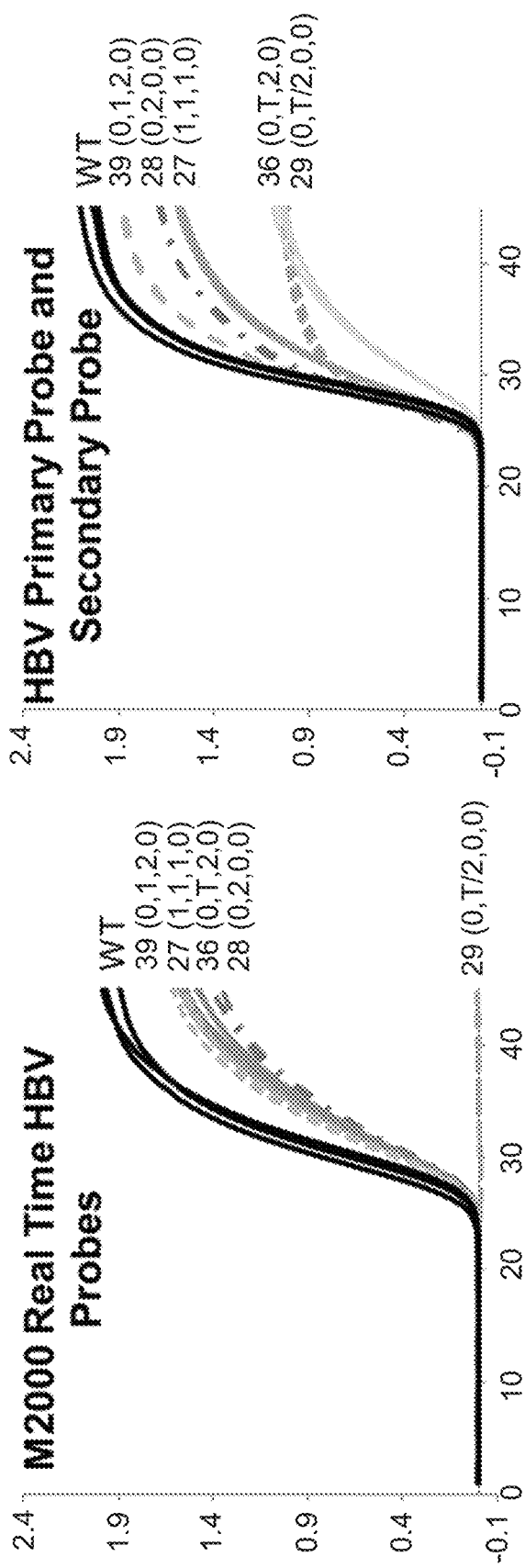

SEQUENCE LISTING

```
<160> NUMBER OF SEQ ID NOS: 7

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
agagtctaga ctcgtggtgg a                                             21

<210> SEQ ID NO 2
<211> LENGTH: 27
<212> TYPE: DNA
<213> ORGANISM: Artificial Sequence
<220> FEATURE:
<223> OTHER INFORMATION: Synthetic

<400> SEQUENCE: 2
aagaagatga ggcatagcag caggatg                                       27

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
tggccaaaat tcgcagtccc                                               20

<210> SEQ ID NO 4
<211> LENGTH: 18
<212> TYPE: DNA
<213> ORGANISM: Artificial Sequence
<220> FEATURE:
<223> OTHER INFORMATION: Synthetic

<400> SEQUENCE: 4
tggatgtgtc tgcggcgt                                                 18
```

```
<210> SEQ ID NO 5
<211> LENGTH: 18
<212> TYPE: DNA
<213> ORGANISM: Artificial Sequence
<220> FEATURE:
<223> OTHER INFORMATION: Synthetic

<400> SEQUENCE: 5
cuucacuuuc ucuugcag                                                 18

<210> SEQ ID NO 6
<211> LENGTH: 23
<212> TYPE: DNA
<213> ORGANISM: Artificial Sequence
<220> FEATURE:
<223> OTHER INFORMATION: Synthetic

<400> SEQUENCE: 6
acaaatttgg aagccatcca tca                                           23

<210> SEQ ID NO 7
<211> LENGTH: 30
<212> TYPE: DNA
<213> ORGANISM: Artificial Sequence
<220> FEATURE:
<223> OTHER INFORMATION: Synthetic

<400> SEQUENCE: 7
aagctgacga gttcatgagg gcaggccgct                                    30
```

ASSAY FOR DETECTING HEPATITIS B VIRUS (HBV)

CROSS-REFERENCE TO RELATED APPLICATIONS

This application claims the benefit of U.S. Provisional Patent Application No. 62/564,008, filed Sep. 27, 2017, which is incorporated by reference herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 1,460 Byte ASCII (Text) file named "2017_09_27_13122USL1-SEQ-LIST.txt," created on Sep. 27, 2017.

BACKGROUND OF THE INVENTION

Hepatitis B virus (HBV) is a DNA virus containing a partially double-stranded genome of approximately 3.2 kb (Liang et al., *Hepatology*, 49(5): S13-21 (2009), Lok et al., *Hepatology*, 34(6):1225-41 (2001), and Hepatitis and Liver Cancer: A National Strategy for Prevention and Control of Hepatitis B and C. Colvin H M, Mitchell A E, Editors. 2010: Washington (DC)). HBV is one of the world's most widespread infectious agents and the most common of several viruses worldwide that can cause lifelong, chronic infection, cirrhosis (scarring) of the liver, liver cancer, liver failure, and death (Liang et al., *Hepatology*, 49(5): S13-21 (2009)). As of 2016, approximately 240 million people globally have chronic hepatitis B and approximately 686,000 people die each year due to complications of hepatitis B, such as cirrhosis and liver cancer (World Health Organization: Media Centre; Hepatitis B Fact Sheet. who.int/mediaventre/factsheets/fs204/en/). A common route of infection is mother-to-child transmission at birth or during early childhood (Gentile et al., *Int J Womens Health*, 6:605-11 (2014), Srivastava et al., *J Pediatric Gastroenterology Nutr*, 59(3): 393-7 (2014), and Yeung et al., *Liver Int*, 30(1):5-18 (2010)). Other risk factors for HBV infection include intravenous drug use, hemophilia, high-risk sexual activity, hemodialysis, needle stick injury in health care staff, and body piercing and tattooing (Schweitzer et al., *Lancet*, 386(10003):1546-1555 (2015)).

HBV has significant genetic diversity within nine known HBV genotypes (A-I), and highly conserved regions. Hepatitis is largely diagnosed via serology (e.g. hepatitis B surface antigen, hepatitis core antigen, and hepatitis B surface antibody). Nucleic acid tests (NATs) for HBV DNA are used as an aid in the management of patients with chronic HBV infection undergoing anti-viral therapy, to measure HBV DNA levels at baseline, and during treatment to aid in assessing response to treatment (Terrault et al., *Hepatology*, 63(1):261-282 (2015)). However, many existing nucleic acid tests utilize a single probe to detect and quantify HBV DNA. Such single-probe detection methods can result in under-quantification or lack of detection of some rare HBV variants and emerging variants due to mutations within the probe region. Nucleic acid tests also are typically performed using PCR reagents provided in liquid format that require frozen storage and batch testing, and turn around-time for sample preparation and real-time PCR can exceed several hours for some tests. NATs also are prone to handling errors such as contamination, and DNA levels can drop below the limit of detection when the initial peak of virus resolves, especially when testing pooled samples.

Thus, there remains a need for HBV detection methods and systems that (i) reliably detect HBV despite significant HBV genetic diversity, (ii) are provided in a format that eliminates or reduces storage requirements and PCR reagent waste, and (iii) may be performed quickly. The present disclosure provides such methods and systems.

BRIEF SUMMARY OF THE INVENTION

The present disclosure provides a set of oligonucleotide sequences for amplifying and detecting a human hepatitis B virus (HBV) nucleic acid sequence in a sample, which comprises: (a) a forward primer oligonucleotide sequence comprising SEQ ID NO: 1; (b) a reverse primer oligonucleotide sequence comprising SEQ ID NO: 2; (c) a first probe oligonucleotide sequence comprising SEQ ID NO: 3; and (d) a second probe oligonucleotide sequence comprising SEQ ID NO: 4, wherein each of the first and second probe oligonucleotide sequences comprises a detectable label. Also provided is a method for detecting human HBV in a sample using the aforementioned set of oligonucleotides.

The present disclosure also provides a kit for detecting human hepatitis B virus (HBV) in a sample comprising: (a) a forward primer oligonucleotide sequence comprising SEQ ID NO: 1; (b) a reverse primer oligonucleotide sequence comprising SEQ ID NO: 2; (c) a first probe oligonucleotide sequence comprising SEQ ID NO: 3; (d) a second probe oligonucleotide sequence comprising SEQ ID NO: 4; (e) reagents for amplifying and detecting nucleic acid sequences; and (f) instructions for use, wherein each of the first and second probe oligonucleotide sequences comprises a detectable label.

The present disclosure further provides a composition comprising oligonucleotide sequences for amplifying and detecting a human hepatitis B virus (HBV) in a sample, which comprises: (a) a forward primer oligonucleotide sequence comprising SEQ ID NO: 1; (b) a reverse primer oligonucleotide sequence comprising SEQ ID NO: 2; (c) a first probe oligonucleotide sequence comprising SEQ ID NO: 3; and (d) a second probe oligonucleotide sequence comprising SEQ ID NO: 4, wherein each of the first and second probe oligonucleotide sequences comprises a detectable label.

BRIEF DESCRIPTION OF THE DRAWINGS

FIGS. 6A and 6B are a series of graphs that depict the results of amplification and detection of an HBsAg target sequence by the Abbott REALTIME™ m2000 HBV system (FIG. 6A) and the set of oligonucleotides described herein (ALINITY$_m$™ HBV system) (FIG. 6B). The x-axis corresponds to RT-PCR cycle number, and the y-axis corresponds to intensity of the FAM signal. In FIG. 6B, the "primary probe" corresponds to SEQ ID NO: 3, and the "secondary probe" corresponds to SEQ ID NO: 4.

DETAILED DESCRIPTION OF THE INVENTION

Figure 1:
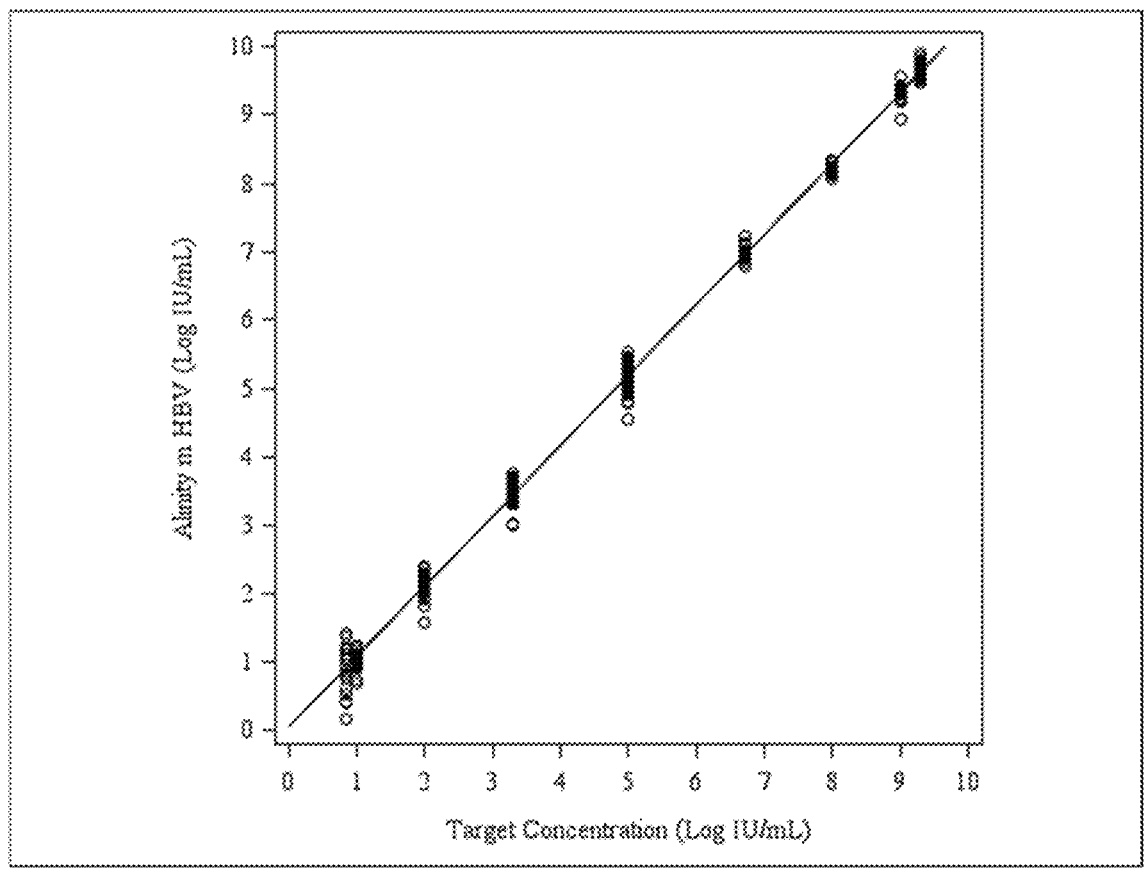
FIG. 1 is a graph which shows that the ALINITY$_m$™ HBV assay is linear from 7 IU/mL to 2,000,000,000 IU/mL with an R value of 0.998 in plasma (for genotype A).

The present disclosure provides a set of oligonucleotides for amplifying and detecting human hepatitis B virus (HBV) in a sample. The term "oligonucleotide," as used herein, refers to a short nucleic acid sequence comprising from about 2 to about 100 nucleotides (e.g., about 5, 10, 15, 20, 25, 30, 35, 40, 45, 50, 55, 60, 65, 70, 75, 80, 85, 90, 95, 99, or 100 nucleotides, or a range defined by any of the foregoing values). The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, for example, methylated and/or capped polynucleotides. Nucleic acids are typically linked via phosphate bonds to form nucleic acid sequences or polynucleotides, though many other linkages are known in the art (e.g., phosphorothioates, boranophosphates, and the like).

Oligonucleotides can be single-stranded or double-stranded, or can contain portions of both double-stranded and single-stranded sequences. The oligonucleotide can be DNA, both genomic and complimentary DNA (cDNA), RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Oligonucleotides can be obtained by chemical synthesis methods or by recombinant methods. A particular oligonucleotide sequence can encompass conservatively modified variants thereof (e.g., codon substitutions), alleles, orthologs, single nucleotide polymorphisms (SNPs), and complementary sequences as well as the sequence explicitly indicated.

Primer and Probe Oligonucleotides

Oligonucleotides are used in a variety of applications in biotechnology, such as, for example, artificial gene synthesis, as polymerase chain reaction (PCR) primers, in DNA sequencing, and as molecular probes. In one embodiment, the oligonucleotides described herein may be used as primers for nucleic acid amplification or as probes for nucleic acid hybridization and detection. The terms "primer," "primer sequence," and "primer oligonucleotide," as used herein, refer to an oligonucleotide which is capable of acting as a point of initiation of synthesis of a primer extension product that is a complementary strand of nucleic acid (all types of DNA or RNA), when placed under suitable amplification conditions (e.g., buffer, salt, temperature and pH) in the presence of nucleotides and an agent for nucleic acid polymerization (e.g., a DNA-dependent or RNA-dependent polymerase). A primer can be single-stranded or double-stranded. If double-stranded, the primer may first be treated (e.g., denatured) to allow separation of its strands before being used to prepare extension products. Such a denaturation step is typically performed using heat, but may alternatively be carried out using alkali, followed by neutralization. The primers of the present disclosure can be of any suitable size, and desirably comprise, consist essentially of, or consist of about 15 to 50 nucleotides, about 20 to 40 nucleotides, or about 22 to 30 nucleotides. The primers of the present disclosure can contain additional nucleotides in addition to those described herein. For example, depending on the type of amplification process employed, primers can include, for example, a restriction endonuclease recognition site 5' to the target binding sequence (see, e.g., U.S. Pat. Nos. 5,270,184 and 5,455,166), or an RNA polymerase promoter linked to the target binding sequence of the primer. A "forward primer" is a primer that hybridizes (or anneals) to a target nucleic acid sequence (e.g., template strand) for amplification. A "reverse primer" is a primer that hybridizes (or anneals) to the complementary strand of the target sequence during amplification. A forward primer hybridizes with a target sequence 5' with respect to a reverse primer.

The terms "probe," "probe sequence," and "probe oligonucleotide," refer to an oligonucleotide that can selectively hybridize to at least a portion of a target sequence under appropriate amplification conditions (e.g., a portion of a target sequence that has been amplified). In general, a probe sequence is identified as being either "complementary" (i.e., complementary to the coding or sense strand (+)), or "reverse complementary" (i.e., complementary to the antisense strand (−)). The probes of the present disclosure can be of any suitable size, and desirably comprise, consist essentially of, or consist of about 10-50 nucleotides, about 12-35 nucleotides, or about 14-25 nucleotides.

As used herein, the terms "set," "primer set," "probe set," and "primer and probe set," refer to two or more oligonucleotide primers which together are capable of priming the amplification of a target sequence or target nucleic acid of interest (e.g., a target sequence within the HBV) and/or at least one probe which can detect the target sequence or target nucleic acid. In certain embodiments, the term "primer set" refers to a pair of primers including a forward primer (or 5' (upstream) primer) that hybridizes with the 5'-end of the target sequence or target nucleic acid to be amplified and a reverse primer (or 3' (downstream) primer) that hybridizes with the complement of the target sequence or target nucleic acid to be amplified. Such primer sets or primer pairs are particularly useful in PCR amplification reactions.

The set of oligonucleotides described herein may be used to amplify and detect a target HBV nucleic acid sequence in a sample. The terms "target sequence" and "target nucleic acid" are used interchangeably herein and refer to a specific nucleic acid sequence, the presence or absence of which is to be detected by the disclosed method. In the context of the present disclosure, a target sequence preferably includes a nucleic acid sequence to which one or more primers will hybridize and from which amplification will initiate. The target sequence can also include a probe-hybridizing region with which a probe may form a stable hybrid under appropriate amplification conditions. A target sequence may be single-stranded or double-stranded. The primer and probe sequences described herein can target any suitable nucleic acid sequence, or combination of sequences, present in the HBV genome. The HBV genome is an enveloped DNA virus that belongs to the Hepadnaviridae family. It contains a small, partially double-stranded (DS), relaxed-circular DNA (rcDNA) genome that replicates by reverse transcription of an RNA intermediate, the pregenomic RNA (pgRNA). The HBV genome is between 3182 and 3248 base pairs (bp) depending on the genotype. The HBV genome encodes four overlapping open reading frames (ORFs) that are translated into viral core protein, surface proteins, polymerase/reverse transcriptase (RT), and Hepatitis B protein x (HBx). At least nine genotypes (A-I) and more than 24 subtypes of HBV have been identified globally.

The set of oligonucleotides described herein may comprise, consist essentially of, or consist of any number of primer and probe oligonucleotides so as to amplify and detect any suitable number of HBV nucleic acid sequences. In one embodiment, the set of oligonucleotides described herein comprises, consists essentially of, or consists of two or more primers which amplify an HBV nucleic acid sequence comprising at least a portion of the HBV surface antigen gene to produce a single HBV amplicon, and at least two probes which hybridize to two different regions of the single HBV amplicon. A "portion" of a nucleic acid sequence comprises at least ten nucleotides (e.g., about 10 to about 5000 nucleotides). Preferably, a "portion" of a nucleic acid sequence comprises 10 or more (e.g., 15 or more, 20 or more, 25 or more, 30 or more, 35 or more, 40 or more, 45 or more, 50 or more, or 100 or more) nucleotides, but less than 5,000 (e.g., 4900 or less, 4000 or less, 3000 or less, 2000 or less, 1000 or less, 800 or less, 500 or less, 300 or less, or 100 or less) nucleotides. As used herein, the term "amplicon" refers to a product of a natural or artificial amplification reaction. In one embodiment, for example, the first target HBV nucleic acid sequence comprises a highly conserved nucleic acid sequence comprising at least a portion of the HBV surface antigen gene.

In one embodiment, the set of oligonucleotides described herein comprises, consists essentially of, or consists of (a) a forward primer oligonucleotide sequence comprising SEQ ID NO: 1; (b) a reverse primer oligonucleotide sequence comprising SEQ ID NO: 2; (c) a first probe oligonucleotide sequence comprising SEQ ID NO: 3; and (d) a second probe oligonucleotide sequence comprising SEQ ID NO: 4 (also referred to as ALINITY$_m$™ HBV).

The set of oligonucleotides described herein comprise a "dual-probe" design, in contrast to other commercially available HBV nucleic acid tests which utilize a single probe to detect and quantify HBV DNA (e.g., Abbott REAL-TIME™ HBV) (Abbott Molecular, Inc., Des Plaines, Ill.; COBAS® HBV for the COBAS® 4800 System (Roche Molecular Diagnostics, Pleasanton, Calif.); COBAS® HBV for the COBAS® 6800/8800 System (Roche Molecular Diagnostics, Pleasanton, Calif.; and VERIS/MDx® HBV Assay (Beckman Coulter, Inc., Brea, Calif.)). The turnaround time for sample preparation and real-time PCR for such "single-probe" detection systems can exceed 6 hours in some instances. In contrast, the amplification and detection methods described herein allow for sample-to-result analysis in approximately two hours starting from a blood specimen. In addition, as discussed above, the set of oligonucleotides described herein enhances reliability of detection of multiple HBV genotypes, as the set amplifies and detects a highly conserved region of the HBV genome.

Any one or combination of the oligonucleotides described herein may be modified in any suitable manner so as to stabilize or enhance the binding affinity (also referred to as "melting temperature" or "$T_m$") of a primer or probe oligonucleotide for its target. In this respect, an oligonucleotide sequence as described herein may comprise one or more modified oligonucleotide bases. For example, the oligonucleotide sequence may comprise one or more propyne-modified bases, wherein the oligonucleotide comprises an alkyne with the chemical formula $CH_3C\equiv CH$. The one or more propyne-modified bases may include, for example, 5-(1-propynyl)-2'-deoxy-Uridine (pdU) and/or 5-(1-propynyl)-2'-deoxyCytidine (pdC).

Any one of the inventive oligonucleotide sequences described herein may comprise, consist essentially of, or consist of a complement of any of the sequences described herein. The terms "complement" or "complementary sequence," as used herein, refer to a nucleic acid sequence that forms a stable duplex with an oligonucleotide described herein via Watson-Crick base pairing rules, and typically shares about 80%, about 81%, about 82%, about 83%, about 84%, about 85%, about 86%, about 87%, about 88%, about 89%, about 90%, about 91%, about 92%, about 93%, about 94% about 95%, about 96%, about 97%, about 98% or about 99% greater identity with the inventive oligonucleotide. Nucleic acid sequence identity can be determined using any suitable mathematical algorithm or computer software known in the art, such as, for example, CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3×, FASTM, and SSEARCH) (for sequence alignment and sequence similarity searches). Sequence alignment algorithms also are described in, for example, Altschul et al., *J. Molecular Biol.*, 215(3): 403-410 (1990); Beigert et al., *Proc. Natl. Acad. Sci. USA*, 106(10): 3770-3775 (2009), Durbin et al., eds., *Biological Sequence Analysis: Probalistic Models of Proteins and Nucleic Acids*, Cambridge University Press, Cambridge, UK (2009); Soding, *Bioinformatics*, 21(7): 951-960 (2005); Altschul et al., *Nucleic Acids Res.*, 25(17): 3389-3402 (1997); and Gusfield, *Algorithms on Strings, Trees and Sequences*, Cambridge University Press, Cambridge UK (1997)).

The oligonucleotides described herein may be prepared using any suitable method, a variety of which are known in the art (see, for example, Sambrook et al., *Molecular Cloning. A Laboratory Manual*, 1989, 2. Supp. Ed., Cold Spring Harbor Laboratory Press: New York, N.Y.; M. A. Innis (Ed.), *PCR Protocols. A Guide to Methods and Applications*, Academic Press: New York, N.Y. (1990); P. Tijssen, *Hybridization with Nucleic Acid Probes—Laboratory Techniques in Biochemistry and Molecular Biology (Parts I and II)*, Elsevier Science (1993); M. A. Innis (Ed.), *PCR Strategies*, Academic Press: New York, N.Y. (1995); and F. M. Ausubel (Ed.), Short Protocols in Molecular Biology, John Wiley & Sons: Secaucus, N.J. (2002); Narang et al., *Meth. Enzymol.*, 68: 90-98 (1979); Brown et al., *Meth. Enzymol.*, 68: 109-151 (1979); and Belousov et al., *Nucleic Acids Res.*, 25: 3440-3444 (1997)). Primer pairs also can be designed using a variety of tools, such as the Primer-BLAST tool provided by the National Center of Biotechnology Information (NCBI). Oligonucleotide synthesis may be performed on oligo synthesizers such as those commercially available from Perkin Elmer/Applied Biosystems, Inc. (Foster City, Calif.), DuPont (Wilmington, Del.), or Milligen (Bedford, Mass.).

Alternatively, oligonucleotides can be custom made and obtained from a variety of commercial sources well-known in the art, including, for example, the Midland Certified Reagent Company (Midland, Tex.), Eurofins Scientific (Louisville, Ky.), BioSearch Technologies, Inc. (Novato, Calif.), and the like. Oligonucleotides may be purified using any suitable method known in the art, such as, for example, native acrylamide gel electrophoresis, anion-exchange HPLC (see, e.g., Pearson et al., *J. Chrom.*, 255: 137-149 (1983)), and reverse phase HPLC (see, e.g., McFarland et al., *Nucleic Acids Res.*, 7: 1067-1080 (1979)).

The sequence of the primers and probes can be verified using any suitable sequencing method known in the art, including, but not limited to, chemical degradation (see, e.g., Maxam et al., *Methods of Enzymology*, 65: 499-560 (1980)), matrix-assisted laser desorption ionization time-of-flight (MALDI-TOF) mass spectrometry (see, e.g., Pieles et al., *Nucleic Acids Res.*, 21: 3191-3196 (1993)), mass spectrometry following a combination of alkaline phosphatase and exonuclease digestions (Wu et al. *Anal. Biochem.*, 290: 347-352 (2001)), and the like.

The primer and probe oligonucleotides described herein desirably comprise a melting temperature ($T_M$) in the range 45° C. to 80° C. In accordance with the present disclosure, the oligonucleotides specifically hybridize to a target HBV nucleic acid sequence without exhibiting significant hybridization to non-HBV nucleic acids. In addition, the oligonucleotides are selected such that they hybridize to conserved regions in the HBV genome, thus minimizing mismatches with the target sequence. This selection ensures that the oligonucleotides are capable of hybridizing to HBV nucleic acids from all genotypes and subtypes. Furthermore, the oligonucleotides are selected such that they show the least likelihood of dimer formation and contain minimal sequence repeats. Such properties can be determined by methods known in the art, for example, using the computer modelling program OLIGO® Primer Analysis Software (distributed by National Biosciences, Inc., Plymouth, Minn.).

Detectable Label

Any one or more of the primer and probe oligonucleotide sequences described herein may comprise a detectable label, such that the primer and/or probe can be visualized, following binding to another entity (e.g., an amplification product or amplicon). The term "detectable label," as used herein, refers to a moiety or compound that generates a signal which can be measured and whose intensity is related to (e.g., proportional to) the amount of entity bound thereto. Any suitable detectable label that can be conjugated or linked to an oligonucleotide in order to detect binding of the oligonucleotide to a target sequence can be used, many of which are known in the art. In one embodiment, the detectable label may be detected indirectly. Indirectly detectable labels are typically specific binding members used in conjunction with a "conjugate" that is attached or coupled to a directly detectable label. Coupling chemistries for synthesizing such conjugates are well-known in the art and are designed such that the specific binding property of the specific binding member and the detectable property of the label remain intact. As used herein, "specific binding member" and "conjugate" refer to the two members of a binding pair, i.e., two different molecules, where the specific binding member binds specifically to the polynucleotide of the present disclosure, and the "conjugate" specifically binds to the specific binding member. Binding between the two members of the pair is typically chemical or physical in nature. Examples of such binding pairs include, but are not limited to, antigens and antibodies, avidin/streptavidin and biotin, haptens and antibodies specific for haptens, complementary nucleotide sequences, enzyme cofactors/substrates and enzymes, and the like.

In another embodiment, the detectable label may be directly detected. Such directly detectable labels include, for example, radioisotopes, fluorophores, chemiluminophores, enzymes, colloidal particles, fluorescent microparticles, intercalating dyes (e.g., SYBR Green or ethidium bromide), and the like. In one embodiment, the detectable label may be a fluorophore, such as a fluorescein-family dye, polyhalofluorescein-family dye, hexachlorofluorescein-family dye, coumarin-family dye, rhodamine-family dye, cyanine-family dye, oxazine-family dye, thiazin-family dye, squaraine-family dye, chelated lanthanide-family dye, azo-family dye, triphenylmethane-family dye, or a BODIPY®-family dye. Examples of fluorophores include, but are not limited to, FAM™, HEX™ JOE™ NED™ PET®, ROX™ TAMRA™, TET™, TEXAS RED®, and VIC®. One skilled in the art will appreciate that directly detectable labels may require additional components, such as substrates, triggering reagents, light, and the like, to enable detection of the label. Methods for labeling oligonucleotides, such as probes, are well-known in the art and described in, e.g., Kricka et al., *Ann. Clin. Biochem.*, 39: 114-129 (2002); van Gijlswijk et al., *Expert Rev. Mol. Diagn.*, 1: 81-91 (2001); Joos et al., *J. Biotechnol.*, 35: 135-153 (1994); Smith et al., *Nucl. Acids Res.*, 13: 2399-2412 (1985); Connoly et al., *Nucl. Acids. Res.*, 13: 4485-4502 (1985); Broker et al., *Nucl. Acids Res.*, 5: 363-384 (1978); Bayer et al., *Methods of Biochem. Analysis*, 26: 1-45 (1980); Langer et al., *Proc. Natl. Acad. Sci. USA*, 78: 6633-6637 (1981); Richardson et al., *Nucl. Acids Res.*, 11: 6167-6184 (1983); Brigati et al., *Virol.*, 126: 32-50 (1983); Tchen et al., *Proc. Natl. Acad. Sci. USA*, 81: 3466-3470 (1984); Landegent et al., *Exp. Cell Res.*, 15: 61-72 (1984); A. H. Hopman et al., *Exp. Cell Res.*, 169: 357-368 (1987); and Temsamani et al., *Mol. Biotechnol.*, 5: 223-232 (1996).

In another embodiment, any one or more of the primer and probe oligonucleotide sequences described herein may also comprise a quencher moiety. When a detectable label (e.g., a fluorophore) and quencher moiety are held in close proximity, such as at the ends of a probe, the quencher moiety prevents detection of a signal (e.g., fluorescence) from the detectable label. When the two moieties are physically separated, such as after cleavage by a DNA polymerase, the signal becomes detectable. The quencher may be selected from any suitable quencher known in the art, such as, for example, BLACK HOLE QUENCHER® 1 (BHQ-1®), BLACK HOLE QUENCHER® 2 (BHQ-2®), IOWA BLACK® FQ, and IOWA BLACK® RQ. For example, the oligonucleotide probe may comprise a FAM fluorophore and a BHQ-1 quencher.

Both the first and second probe oligonucleotide sequences desirably comprise a detectable label. Each of the probes may be labeled with the same detectable label or different detectable labels. When both probes comprise the same detectable label (e.g., FAM), amplification of the HBV target sequence is detected as a single signal during real-time PCR. When each probe comprises a different detectable label, amplification of the HBV target sequence is detected as two separate signals.

The selection of a particular labeling technique will depend on several factors, such as the ease and cost of the labeling method, spectral spacing between different detectable labels used, the quality of sample labeling desired, the effects of the detectable moiety on the hybridization reaction (e.g., on the rate and/or efficiency of the hybridization process), the nature of the amplification method used, the nature of the detection system, the nature and intensity of the signal generated by the detectable label, and the like.

Internal Control

The set of oligonucleotides for detecting HBV described above may further comprise primer and probe oligonucleotide sequences for amplifying and detecting an internal control (IC) sequence. In one embodiment, the internal control sequences are added to each sample preparation reaction. The internal control is then processed through the entire sample preparation and amplification procedure along with the test samples, controls and calibrators (if present), to demonstrate proper sample processing and assay validity. The internal control may be any suitable non-HBV nucleic acid sequence, including, for example, a nucleic acid sequence encoding GAPDH, beta2-mciroglobulin, beta-actin, R18, or 16S RNA. In one embodiment, for example, the internal control may comprise an DNA sequence derived or obtained from the hydroxypyruvate reductase gene of the pumpkin plant, *Curcurbita pepo*. In this regard, the set of oligonucleotides described herein may further comprise an internal control forward primer oligonucleotide sequence comprising SEQ ID NO: 5, an internal control reverse primer oligonucleotide sequence comprising SEQ ID NO: 6, and an internal control probe oligonucleotide sequence comprising SEQ ID NO: 7. The internal control probe desirably comprises a detectable label, such as any of those described herein. In one embodiment, the internal control probe may comprise a different label than the probes used to detect HBV, which allows for simultaneous detection and differentiation of internal control and HBV-amplified products within the same reaction. The internal control probe may also comprise a quencher moiety, such as those described herein.

Method for Amplifying and Detecting Human Hepatitis B Virus

The present disclosure provides a method for detecting human hepatitis B virus (HBV) in a sample suspected of containing HBV. The method comprises: (a) contacting a sample obtained from a human with the set of oligonucleotide sequences described herein and reagents for amplification and detection of nucleic acid sequences, (b) amplifying a first target HBV nucleic acid sequence present in the sample, (c) hybridizing the first and second oligonucleotide probes to the first target HBV nucleic acid sequence, (d) detecting hybridization of the first and second probe oligonucleotide sequences to the first target HBV nucleic acid sequence by assessing a signal from each of the detectable labels, whereby (i) the presence of the signals indicates hybridization of the first and second probe oligonucleotide sequences to the first target HBV nucleic acid sequence and the presence of HBV in the sample, and (ii) the absence of the signals indicates the absence of HBV in the sample. Descriptions of the primer and probe oligonucleotides set forth herein with respect to the aforementioned set of oligonucleotides also are applicable to those same aspects of the inventive method.

A sample, as defined herein, is "suspected" of containing HBV if the sample is obtained from a subject, preferably a human, suspected of being infected with HBV. A subject is suspected of being infected with HBV if the subject has an increased risk for HBV. An infant born to a mother infected with HBV is at a high risk of HBV infection. Other high-risk factors for HBV infection include, for example, intravenous drug use, hemophilia, high-risk sexual activity, hemodialysis, needle stick injury in health care staff, and body piercing and tattooing.

The sample can be any suitable sample obtained from any suitable subject, typically a mammal (e.g., a human). The sample may be obtained from any biological source, such as, a cervical, vaginal or anal swab or brush, or a physiological fluid including, but not limited to, whole blood, serum, plasma, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen, and the like. The sample can be obtained from the subject using routine techniques known to those skilled in the art, and the sample may be used directly as obtained from the biological source or following a pretreatment to modify the character of the sample. Such pretreatment may include, for example, preparing plasma from blood, diluting viscous fluids, filtration, precipitation, dilution, distillation, mixing, concentration, inactivation of interfering components, the addition of reagents, lysing, etc.

After the sample is obtained from a subject, the sample may be contacted with the set of oligonucleotides comprising forward and reverse primers and first and second probes as described herein to form a reaction mixture. The reaction mixture is then placed under amplification conditions. The primers hybridize to a first target HBV nucleic acid sequence (e.g., at least a portion of the HBV surface antigen gene) if present in the sample, and a first target HBV nucleic acid sequence present in the sample is amplified.

Amplifying an HBV nucleic acid sequence in the sample can be performed using any suitable nucleic acid sequence amplification method known in the art, including but not limited to, polymerase chain reaction (PCR), reverse-transcriptase PCR (RT-PCR), real-time PCR, transcription-mediated amplification (TMA), rolling circle amplification, nucleic acid sequence based amplification (NASBA), strand displacement amplification (SDA), and ligase chain reaction (LCR).

Because HBV comprises a DNA genome, amplification of the HBV virus nucleic acid sequence desirably is performed using PCR, and preferably real-time PCR, in which complimentary DNA (cDNA) fragments are synthesized from a substrate DNA template. The reaction typically involves the use of a synthetic oligonucleotide primer, which is complementary to nucleotide sequences in the substrate DNA, and the use of a DNA polymerase enzyme. The reaction consists of one cycle, in which the oligonucleotide primers, which are present in vast excess, hybridize to the substrate DNA to form double-stranded structures along complementary nucleotide sequences. The primer-substrate DNA:DNA complexes will then serve as initiation sites for a cDNA synthesis reaction catalyzed by DNA polymerase, resulting in the synthesis of a cDNA strand complementary to the DNA strand. "Real-time PCR," as used herein, refers to a PCR method in which the accumulation of amplification product is measured as the reaction progresses, in real time, with product quantification after each cycle, in contrast to conventional PCR in which the amplified DNA product is detected in an end-point analysis. Real-time PCR also is known in the art at "quantitative PCR (qPCR)." Real-time detection of PCR products typically involves the use of non-specific fluorescent dyes that intercalate with any double-stranded DNA and sequence-specific fluorescently-labeled DNA probes. Real-time PCR techniques and systems are known in the art (see, e.g., Dorak, M. Tevfik, ed. *Real-time PCR*. Taylor & Francis (2007); and Fraga et al., "Real-time PCR," *Current protocols essential laboratory*

*techniques:* 10-3 (2008)) and are commercially available from a variety of sources (e.g., m2000rt REALTIME™ PCR system (Abbott Molecular, Inc., Des Plaines, Ill.); CFX Real-Time PCR Detection Systems (Bio-Rad Laboratories, Inc., Hercules, Calif.); and TAQMAN™ Real-Time PCR System (ThermoFisher Scientific, Waltham, Mass.)), any of which can be employed in the methods described herein.

Following amplification of an HBV virus nucleic acid sequence (e.g., at least a portion of the HBV surface antigen gene) that is present in the sample, the inventive method further comprises hybridizing the first and second probe oligonucleotides to the target HBV nucleic acid sequence. In one embodiment, a reaction mixture comprising an HBV amplicon may be contacted with the first and second oligonucleotide probes, as described herein, that preferentially hybridize to a target nucleic acid sequence of the amplicon, or the complement thereof, under stringent hybridization and wash conditions, thereby forming a hybrid duplex that is stable for detection. "Hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. "Stringent hybridization conditions" as used herein means conditions under which hybridization of fully complementary nucleic acid strands is strongly preferred. Under stringent hybridization conditions, a first nucleic acid sequence (for example, a primer) will hybridize to a second nucleic acid sequence (for example, a target sequence), such as in a complex mixture of nucleic acids. Stringent conditions are sequence-dependent and will be different in different circumstances. Stringent conditions can be selected to be about 5-10° C. lower than the thermal melting point ($T_m$) for the specific sequence at a defined ionic strength pH. The $T_m$ can be the temperature (under defined ionic strength, pH, and nucleic concentration) at which 50% of an oligonucleotide complementary to a target hybridize to the target sequence at equilibrium (as the target sequences are present in excess, at $T_m$, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C. Any suitable method and conditions for hybridizing the first and second oligonucleotide probes to the target HBV nucleic acid sequence known in the art can be used in the inventive method.

Following hybridization of the first and second probe oligonucleotide sequences to the target HBV nucleic acid sequence, the method comprises detecting hybridization of the first and second probe oligonucleotide sequences to the target HBV nucleic acid sequence by assessing a signal from each of the detectable labels, whereby (i) the presence of the signals indicates hybridization of the first and second probe oligonucleotide sequences to the first target HBV nucleic acid sequence and the presence of HBV in the sample, and (ii) the absence of the signals indicates the absence of HBV in the sample. Detection of signals from the first and second probes may be performed using a variety of well-known methodologies, including, for example homogeneous or heterogeneous techniques.

Homogeneous detection methods involve detecting products of the amplification reaction as they are formed, namely, in a real time manner. As a result, amplification product/probe hybrids are formed and detected while the reaction mixture is under amplification conditions. Homogeneous detection methods include, but are not limited to, the use of FRET labels that are attached to the probes and that emit a signal in the presence of the target sequence, Molecular Beacons (See, Tyagi et al., *Nature Biotechnol.*, 14: 303-308 (1996); Tyagi et al., *Nature Biotechnol.*, 16: 49-53 (1998); Kostrikis et al., *Science*, 279: 1228-1229 (1998); Sokol et al., *Proc. Natl. Acad. Sci. USA*, 95: 11538-11543 (1998); Marras et al., *Genet. Anal.*, 14: 151-156 (1999); and U.S. Pat. Nos. 5,846,726, 5,925,517, 6,277,581 and 6,235,504), TAQMAN® assays (see, e.g., U.S. Pat. Nos. 5,210,015; 5,804,375; 5,487,792 and 6,214,979 and International Patent Application Publication WO 01/86001), and hybridization protection assays (HPA) which utilize probes labeled with acridinium ester (AE) (see, e.g., Weeks et al., *Clin. Chem.*, 29: 1474-1479 (1983); Berry et al., *Clin. Chem.*, 34: 2087-2090 (1988)).

Heterogeneous detection systems generally employ a capture agent to separate amplified sequences from other materials in the reaction mixture. Capture agents typically comprise a solid support material (e.g., microtiter wells, beads, chips, and the like) coated with one or more specific binding sequences. A binding sequence may be complementary to a tail sequence added to oligonucleotide probes of the disclosure. Alternatively, a binding sequence may be complementary to a sequence of a capture oligonucleotide, itself comprising a sequence complementary to a tail sequence of a probe. After separation of the amplification product/probe hybrids bound to the capture agents from the remaining reaction mixture, the amplification product/probe hybrids can be detected using any suitable detection method known in the art or described herein.

Kits and Compositions for Amplifying and Detecting a Hepatitis B Virus Nucleic Acid Sequence The disclosure also provides a kit for amplifying and detecting human HBV in a sample. The kit comprises a forward primer oligonucleotide, a reverse primer oligonucleotide, a first probe oligonucleotide comprising a detectable label, a second probe oligonucleotide comprising a detectable label, and reagents and instructions for amplifying and detecting HBV. Descriptions of the primer oligonucleotides and probe oligonucleotides set forth herein with respect to the aforementioned methods also are applicable to those same aspects of the kits described herein. Examples of suitable reagents for inclusion in the kit (in addition to the oligonucleotide primers and probes described herein) include conventional reagents employed in nucleic acid amplification reactions, such as, for example, one or more enzymes having polymerase activity, enzyme cofactors (such as magnesium or nicotinamide adenine dinucleotide (NAD)), salts, buffers, deoxyribonucleotide, or ribonucleotide triphosphates (dNTPs/rNTPs; for example, deoxyadenosine triphosphate, deoxyguanosine triphosphate, deoxycytidine triphosphate, and deoxythymidine triphosphate) blocking agents, labeling agents, and the like. Many such reagents are described herein or otherwise known in the art and commercially available. The kit may contain multi-well assay trays. The kit may contain two multi-well assay trays, one may contain lyophilized, unit-dose RT-PCR amplification/detection reagents and lyophilized, unit-dose internal control, and proteinase K in separate wells, and the other may contain liquid activation reagent.

In one embodiment, the kit may comprise, consist essentially of, or consist of (a) a forward primer oligonucleotide sequence comprising SEQ ID NO: 1; (b) a reverse primer oligonucleotide sequence comprising SEQ ID NO: 2; (c) a first probe oligonucleotide sequence comprising SEQ ID NO: 3; (d) a second probe oligonucleotide sequence comprising SEQ ID NO: 4; (e) reagents for amplifying and detecting nucleic acid sequences; and (f) instructions for use, wherein each of the first and second probes comprises a detectable label.

The kit may comprise instructions for using the amplification reagents and primer and probe oligonucleotides described herein, e.g., for processing the test sample, extracting nucleic acid molecules, and/or performing the test; and for interpreting the results obtained, as well as a notice in the form prescribed by a governmental agency. Such instructions optionally can be in printed form or on CD, DVD, or other format of recorded media.

The present disclosure also provides a composition for amplifying and detecting HBV in a sample. The composition comprises, consists essentially of, or consists of a forward primer oligonucleotide, a reverse primer oligonucleotide, a first probe oligonucleotide comprising a detectable label, and a second probe oligonucleotide comprising a detectable label. Descriptions of the primer oligonucleotides and probe oligonucleotides set forth herein with respect to the aforementioned methods and kit also are applicable to those same aspects of the composition described herein. In some embodiments, the composition comprises a carrier, preferably a pharmaceutically (e.g., physiologically acceptable) carrier. Any suitable carrier can be used within the context of the invention, and such carriers are well known in the art. The composition can optionally be sterile or sterile with the exception of the oligonucleotides described herein.

The aforementioned kit and composition may further comprise primer and probe oligonucleotides that amplify and detect an internal control nucleic acid sequence, as described herein. In this regard, the kit and/or composition may comprise an internal control forward primer oligonucleotide sequence comprising SEQ ID NO: 5, an internal control reverse primer oligonucleotide sequence comprising SEQ ID NO: 6, and an internal control probe oligonucleotide sequence comprising SEQ ID NO: 7 which comprises a detectable label.

The kits and/or composition may be supplied in a solid (e.g., lyophilized) or liquid form. In one embodiment, the primer oligonucleotides, probe oligonucleotides, and other reagents are lyophilized (i.e., freeze dried). As discussed above, many single-target HBV detection systems known in the art provide PCR reagents in liquid format that requires frozen storage and batch testing. Lyophilization of the various components of the kit and composition described herein, however, eliminates the need for frozen storage and allows the assay components to be delivered in unit-dose format such that users may run the exact number of assays required, thereby minimizing reagent waste. The various components of the kits and composition of the present invention may optionally be contained within different containers (e.g., vial, ampoule, test tube, flask, or bottle) for each individual component (e.g., primer oligonucleotides, probe oligonucleotides, or buffer). Each component will generally be suitable as aliquoted in its respective container or provided in a concentrated form. Other containers suitable for conducting certain steps of the amplification/detection assay may also be provided. The individual containers are preferably maintained in close confinement for commercial sale.

The following examples further illustrate the invention but, of course, should not be construed as in any way limiting its scope.

EXAMPLE 1

This example demonstrates a method for amplifying and detecting human HBV in a sample in accordance with the present disclosure.

An HBV detection assay that utilizes real-time PCR to amplify and detect HBV DNA genomic sequences extracted from human plasma or serum specimens has been developed by Abbott Molecular, Inc. (Des Plaines, Ill.) under the brand name ALINITY$_m$™ HBV. The assay is intended to be used (1) to assess disease prognosis by measuring the baseline HBV level and to assess viral response to antiretroviral treatment by measuring changes of HBV DNA levels in serum or plasma; and (2) as an aid in the diagnosis of HBV infection and to confirm HBV infection in plasma or serum from individuals that have reactive results with HBV immunoassays.

The ALINITY$_m$™ HBV assay consists of sample preparation, RT-PCR assembly, amplification/detection, and result calculation and reporting. All stages of the ALINITY$_m$™ HBV assay procedure are executed automatically by the ALINITY$_m$™ instrument. HBV DNA from human plasma or serum is extracted automatically on-board the Abbott ALINITY$_m$™ instrument using the ALINITY$_m$™ Sample Prep Kit 2, ALINITY$_m$™ Lysis Solution, and ALINITY$_m$™ Diluent Solution, which employ magnetic microparticle technology to facilitate nucleic acid capture, wash, and elution.

At the beginning of the ALINITY$_m$™ sample preparation process, a lyophilized internal control at 1× (containing linearized plasmid DNA) and proteinase K is automatically rehydrated on the assay plate by the ALINITY$_m$™ instrument and delivered into each sample preparation reaction. The internal control linearized plasmid consists of purified plasmid DNA containing a 566 bp portion of the hydroxypyruvate reductase gene of the pumpkin plant, *Cucurbita*

*pepo*, which is unrelated to HBV, cloned into vector pBlue-Script KS-. The purified plasmid is cut with the restriction enzyme Bgl I which creates 2 fragments of molecular weight 1267 bp and 2251 bp. Proteinase K (pK) is a subtilisin-related serine protease that digests proteins efficiently. pK is used to assist in lysing the viral particle, to remove the HBV polymerase that is covalently attached to the HBV DNA genome, and to inactivate endogenous nucleases and other interfering proteins during sample preparation.

The internal control and pK are then processed through the entire sample preparation and PCR procedure along with the specimens, calibrators, and controls to demonstrate proper sample processing and assay validity. The internal control reagent is prepared by mixing excipient, pK and 2× internal control bulk (consisting of non-infectious internal control target plasmid DNA in TE buffer). The formulation of the internal control is set forth in Table 1 below.

TABLE 1

Internal Control Formulation

| Component | Component Concentration (pre-lyophilization) |
|---|---|
| Internal Control - target at 1X | Diluted from 2X IC at $1.22^{e}5$ IU/mL |
| TE Buffer with poly-dA:dT | NA |
| Trehalose | 6.32% (as excipient) |
| Lyophilized pK (rehydrated with water) | 1.0 chromozyme units/reaction |

The PCR master mix reagent is prepared by combining KAPA2G DNA Polymerase, UDG, excipient, forward and reverse oligonucleotide primers (as described herein), first and second oligonucleotide probes (as described herein), molecular biology grade water, PCR buffer components, dNTPs, and Cal610 passive reference dye.

KAPA2G Polymerase is an engineered enzyme for higher processivity and speed through directed evolution, which offers significantly faster extension rates than wild-type TAQ® DNA polymerase. KAPA2G has a highly processive 5'-3' DNA polymerase but lacks 3'-5' exonuclease activity. Uracil-DNA Glycosylase (UDG) catalyzes the release of free uracil from uracil-containing DNA and provides a means of contamination control for external amplicons containing uracil.

The master mix formulation is set forth in Table 2.

TABLE 2

Mastermix Reagent Formulation

| Component | Reaction Concentration |
|---|---|
| HBV Forward Primer | 300 nM |
| HBV Reverse Primer | 1.30 µM |
| HBV Probe (FAM) | 45.5 nM |
| HBV Probe2 (FAM) | 45.5 nM |
| IC Forward Primer | 300 nM |
| IC Reverse Primer | 150 nM |
| IC Probe (Q670) | 100 nM |
| dNTPs | 1.3 mM |
| Cal Fluor Red C610 Passive Reference dye | 25 nM |
| Tris-HCl, pH 8.5 | 50 mM |
| Tween-20 | 0.01% (V/V) |
| Gelatin (Fish skin) | 0.01% (W/V) |
| Ficoll 400 | 1.81% (W/V) |
| Ficoll 70 | 1.81% (W/V) |
| Melezitose | 0.60% (W/V) |
| Trehalose | 1.81% (W/V) |
| Kapa 2 G polymerase | 2.9 units/reaction |
| Afu Uracil-DNA Glycosylase (UDG) | 0.3 units |

The master mix reagent and internal control reagent are each prepared in bulk and filled as unit-dose aliquots in multi-well reagent plates. The assembled assay reagent plate is then lyophilized/dried, foil-sealed in a dry environment, labeled, and further packaged with desiccants and sealed into foil pouches.

Liquid activation reagent is prepared by mixing molecular biology grade water, magnesium chloride, and tetramethyl ammonium chloride (TMAC). The formulation of the liquid activation reagent is shown in Table 3. The activator reagent is prepared in bulk and filled as unit-dose in a separate multi-well reagent plate, but the activator reagent is not lyophilized.

TABLE 3

Liquid Activation Reagent Formulation

| Component | Component Concentration (in 21 µL PCR) |
|---|---|
| (Magnesium Chloride) $MgCl_2$ | 13 mM |
| Tetramethyl Ammonium Chloride (TMAC) | 120 mM |

The real-time PCR cycling conditions used by the ALINITY$_m$™ HBV assay are set forth in Table 4.

TABLE 4

Real-Time PCR Cycling Conditions

| Step | Description | Cycles | Temp. (C.°) | Dwell + overshoot (sec.) | Ramp Rate (C.°/sec) |
|---|---|---|---|---|---|
| 1 | UDG activity | 1 | 37.6 | 528.36 + 2.90 | 10 |
| 2 | Hot Start | 1 | 95 | 70.50 | 10 |
| 3 | Thermal mixer | 1 | 70 | 240.00 | 8 |
| 4 | Melt | 1 | 95 | 71.5 | 10 |
| 5 | Amplification/Detection | 45 | 95 | 02.50 + 8.10 | 10 |
|  |  |  | 61 | 25.30 + 4.45 (read) | 8 |

The PCR formulation and cycling conditions described above may be further modified to optimize the assay.

An HBV calibration curve is required for determination of HBV DNA concentration. To this end, two levels of calibrators were processed through sample preparation and PCR to generate the calibration curve. The concentration of HBV DNA in specimens and controls was then calculated from the stored calibration curve. A wild-type (WT) HBV plasmid was prepared consisting of purified plasmid DNA containing the entire HBV genome cloned into vector pSP72. The purified plasmid was cut with the restriction enzyme BamHI, generating three fragments of molecular weight 1372 bp, 1852 bp, and 3082 bp. The inactivated HBV positive stock consists of a high titer HBV positive patient plasma sample which was diluted in negative plasma to an approximate concentration of $1\times10^7$ copies/mL and then heat-inactivated to reduce infectivity.

Assay controls were tested at or above an established minimum frequency to ensure that instrument and reagent performance remained satisfactory. During each control event, a negative control, a low-positive control, and a high-positive control were processed through sample preparation and PCR procedures that are identical to those used for specimens.

The limit of detection (LOD) was determined by testing dilutions of 3rd World Health Organization (WHO) International Standard for Hepatitis B Virus for Nucleic Acid Amplification Techniques (NIBSC code: 10/264; genotype A) prepared in HBV negative human plasma and serum. Testing for each HBV DNA concentration was performed with 4 lots of amplification reagents across multiple days. The results, representative of the analytical sensitivity performance of Alinity m HBV, are summarized for plasma (Table 5) and serum (Table 6).

TABLE 5

Alinity m HBV Limit of Detection (LOD) in Plasma

| HBV DNA Concentration (IU/mL) | Number of Valid Replicates | Number of Replicates Detected | Detection Rate (%) |
|---|---|---|---|
| 15.00 | 94 | 92 | 97.9 |
| 10.0 | 95 | 95 | 100.0 |
| 7.00 | 95 | 92 | 96.8 |
| 4.00 | 94 | 80 | 85.1 |
| 2.00 | 93 | 63 | 67.7 |
| 1.00 | 95 | 39 | 41.1 |
| 0.50 | 94 | 18 | 19.1 |

Probit analysis of the data determined that the concentration of HBV DNA in plasma detected with 95% probability was 6.72 IU/mL (95% CI 5.28 to 9.27 IU/mL).

TABLE 6

Alinity m HBV Limit of Detection (LOD) in Serum

| HBV DNA Concentration (IU/mL) | Number of Valid Replicates | Number of Replicates Detected | Detection Rate (%) |
|---|---|---|---|
| 15.00 | 96 | 95 | 99.0 |
| 10.0 | 95 | 91 | 95.8 |
| 7.00 | 95 | 89 | 93.7 |
| 4.00 | 96 | 83 | 86.5 |
| 2.00 | 93 | 59 | 63.4 |
| 1.00 | 92 | 47 | 51.1 |
| 0.50 | 94 | 35 | 37.2 |

Probit analysis of the data determined that the concentration of HBV DNA in serum detected with 95% probability was 9.62 IU/mL (95% CI 7.14 to 14.43 IU/mL).

Figure 2:
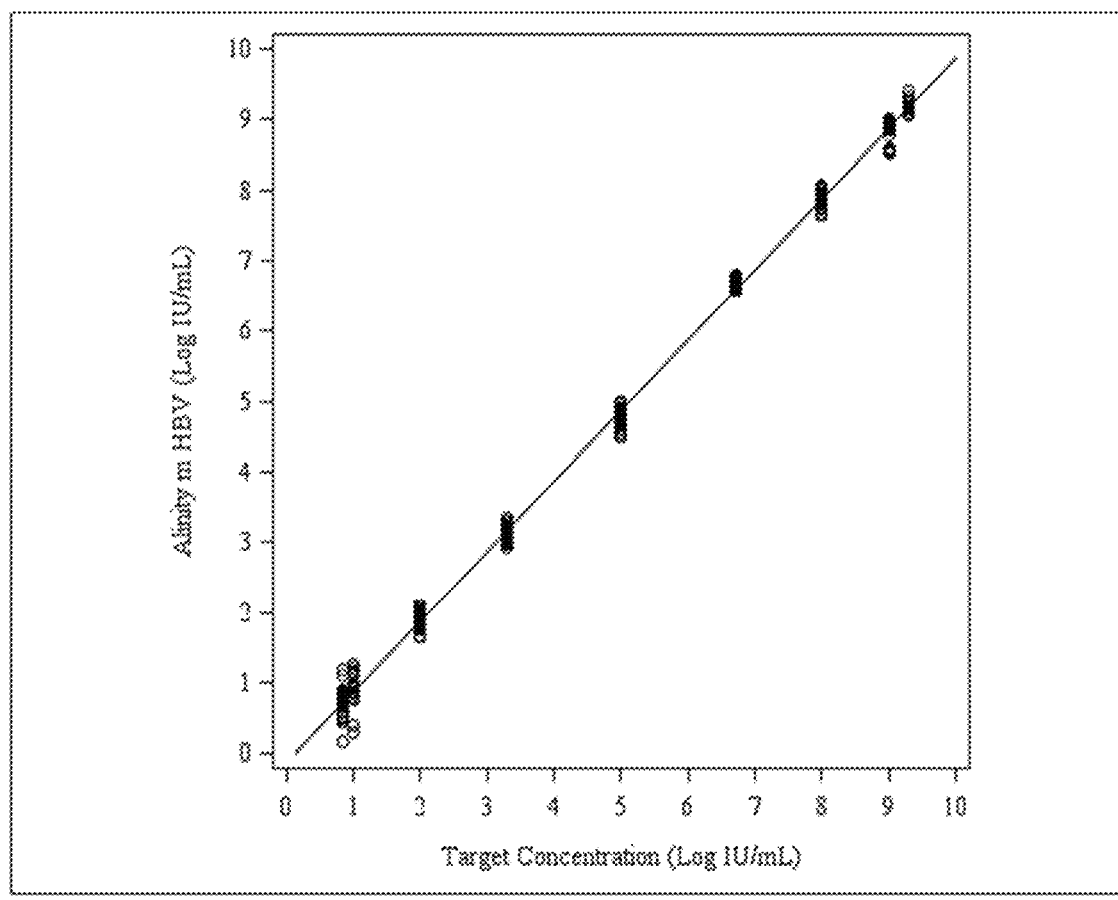
FIG. 2 is a graph which shows that the ALINITY$_m$™ HBV assay is linear from 7 IU/mL to 2,000,000,000 IU/mL with an R value of 0.999 in serum (for genotype A).

The ALINITY$_m$™ HBV assay was linear from 7 IU/mL to 2,000,000,000 IU/mL with an R value of 0.998 for plasma (FIG. 1) and an R value of 0.999 for serum (FIG. 2), as shown in Table 7. Specifically, linearity was evaluated by testing 9 panel levels that bracketed and spanned the intended dynamic range of the assay (10 to $10^9$ IU/mL), including a level targeting the expected Lower Limit of Quantification (LLOQ) at 10 IU/mL and a level equal to the expected Upper Limit of Quantification (ULOQ) at $10^9$ IU/mL. In addition, 2 serum panel levels were prepared at two times the expected ULOQ and one level below LLOQ were included in testing. A minimum of 24 replicates of each panel level were tested.

Figure 3:
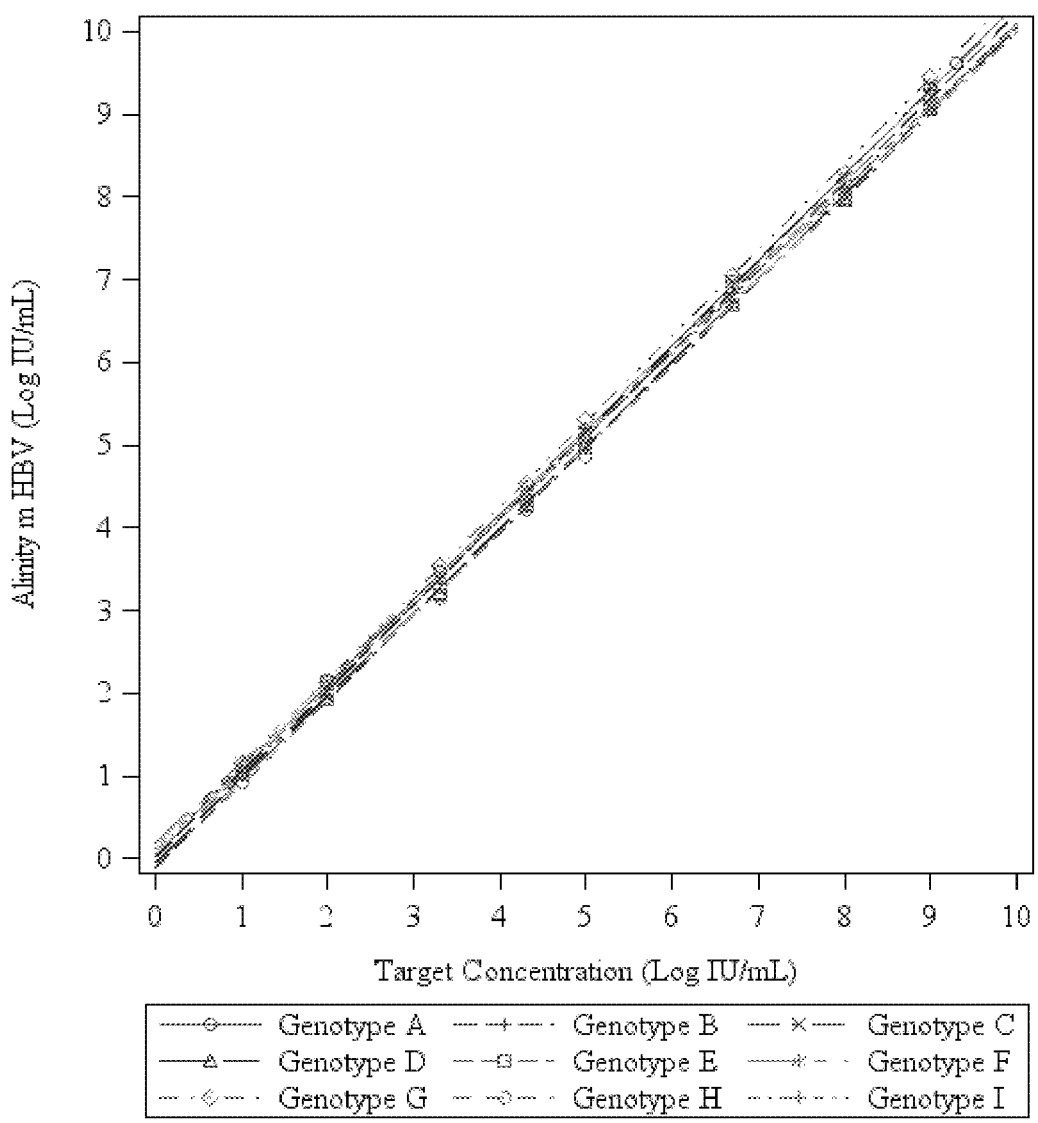
FIG. 3 is a graph which shows that the ALINITY$_m$™ HBV assay is linear from 10 IU/mL to 1,000,000,000 IU/mL in plasma for HBV genotypes B, C, D, E, F, G, H and I.
Figure 4:
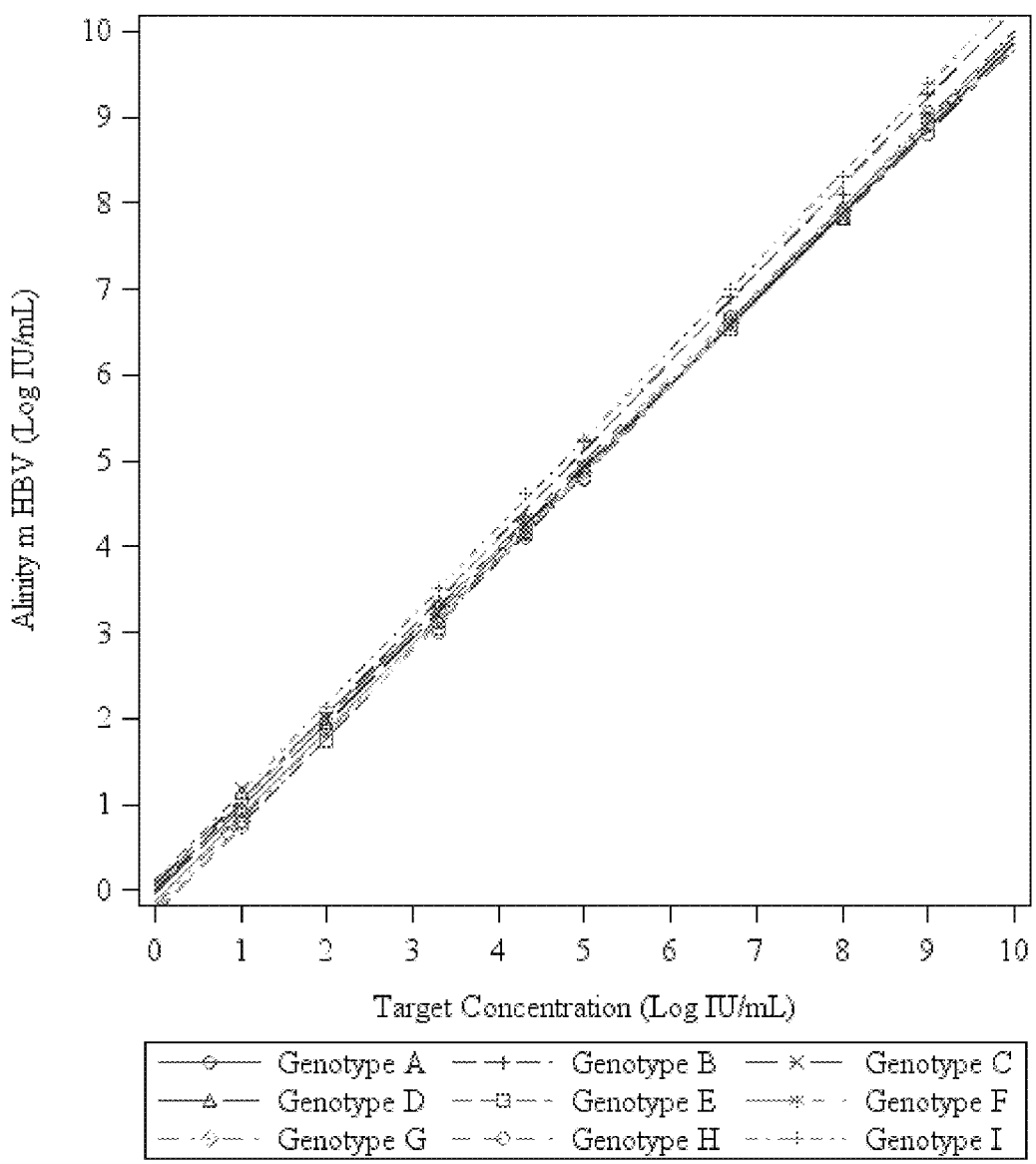
FIG. 4 is a graph which shows that the ALINITY$_m$™ HBV assay is linear from 10 IU/mL to 1,000,000,000 IU/mL in serum for HBV genotypes B, C, D, E, F, G, H and I.

The ALINITY$_m$™ HBV assay was linear from 10 IU/mL to 1,000,000,000 IU/mL for genotypes B, C, D, E, F, G, H, and I in plasma (FIG. 3) and in serum (FIG. 4).

TABLE 7

Linearity of ALINITY$_m$ ™ HBV assay for Serum Samples

| | Plasma | Serum |
|---|---|---|
| Sample Size (n) | 286 | 286 |
| Correlation Coefficient (r) | 0.998 | 0.999 |
| Slope | 1.03 | 1.00 |
| 95% CI for Slope | (1.02, 1.03) | (0.99, 1.01) |
| Intercept | 0.06 | −0.13 |
| 95% CI for Intercept | (0.02, 0.09) | (−0.17, −0.10) |

During lyophilization cycles development, lyophilized amplification reagents were tested across multiple positions from the lyophilizer. The precision and detection for samples at LOD and 10×LOD are shown in Table 8. Ct (threshold cycle) is a relative measure of the concentration of target in the PCR reaction.

TABLE 8

Precision and Detection of Samples

| Sample | N | Detection | Mean HBV Ct | HBV Ct SD | Mean IC Ct | IC Ct SD |
|---|---|---|---|---|---|---|
| LOD | 209 | 100% | 31.04 | 0.28 | 28.76 | 0.35 |
| 10X LOD | 210 | 99.5% | 34.09 | 0.58 | 28.75 | 0.37 |

Figure 5:
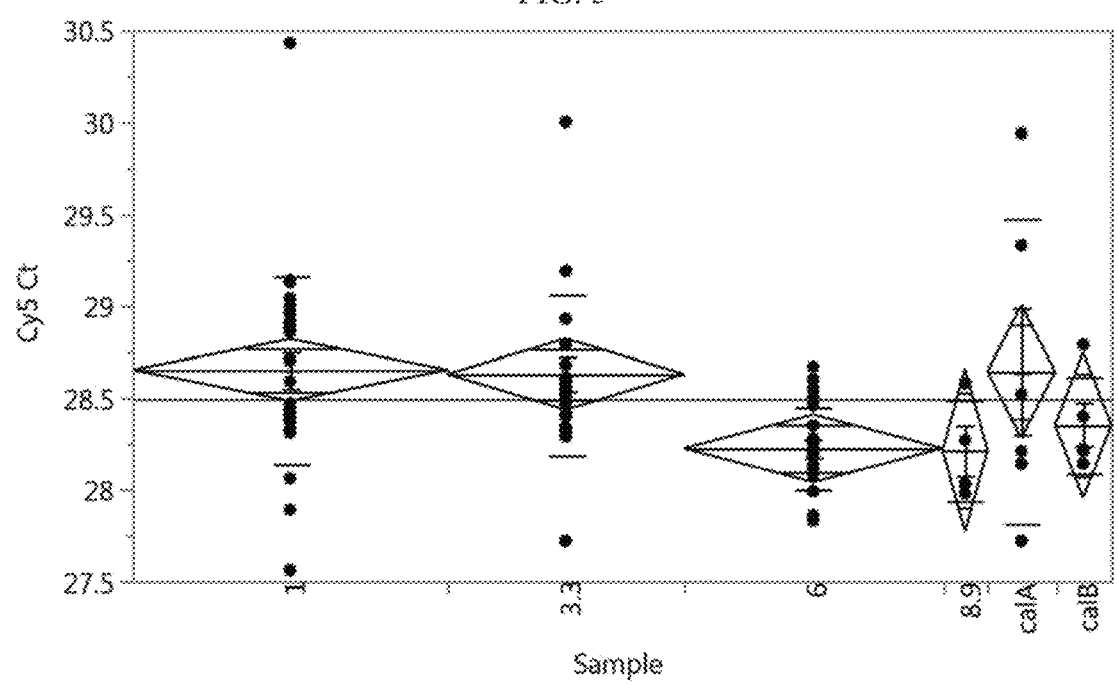
FIG. 5 is a graph that depicts internal control (IC) signal robustness within the linear range of HBV viral load.

Internal control (IC) signal robustness within linear range of HBV viral load was examined using the same target levels as tested in the linearity study described above. The delta IC Ct between the two calibrators was about 0.3 Ct. The delta IC Ct between HBV samples at 3.3 to 6 log IU/mL (which is close to the two calibrators target concentrations) was about 0.4 Ct. The delta IC Ct was similar between calibrators and samples (FIG. 5), as shown in Table 9.

TABLE 9

IC Signal Robustness within linear range of HBV viral load.

| Level | Number | Mean | Standard Deviation | Delta Ct |
|---|---|---|---|---|
| 1 | 28 | 28.65 | 0.52 | |
| 3.3 | 21 | 28.63 | 0.44 | 0.41 |
| 6 | 23 | 28.22 | 0.23 | |
| 8.9 | 4 | 28.22 | 0.27 | |
| calA | 6 | 28.64 | 0.83 | 0.29 |
| calB | 5 | 28.35 | 0.26 | |

The results of this example demonstrate a method of amplifying and detecting HBV in a sample using the set of oligonucleotides described herein.

EXAMPLE 2

This example describes amplification and detection of an HBV nucleic acid sequence using the ALINITY$_m$ HBV™ system described herein as compared to the Abbott REALTIME™ m2000 HBV detection system.

Like the ALINITY$_m$™ HBV system described herein, the Abbott REALTIME™ m2000 HBV system targets the HBV surface antigen gene (HbsAg) and utilizes two probes. The oligonucleotide primers and probes utilized in the REALTIME™ m2000 HBV detection system are described in detail in U.S. Pat. No. 7,015,317. The ALINITY$_m$™ HBV and the REALTIME™ m2000 HBV systems share the same forward and reverse primer oligonucleotides, but the first and second probe oligonucleotide sequences of the ALINITY$_m$™ HBV system are different than those used in the m2000 system.

Using GBLOCKS® Gene Fragments (Integrated DNA Technologies, Inc., Coralville, Iowa) (also referred to herein as "geneblocks") containing mutations at different locations in the primers/probes, amplification and detection of the HBsAg target sequence by the ALINITY$_m$™ HBV system was compared to the m2000 system, as illustrated in FIG. 6. GBLOCKs® Gene Fragments are sequence-verified genomic blocks that have high sequence fidelity which can be used for rapid gene construction or modification, or other applications requiring double-stranded DNA. In particular, synthetic double stranded target sequences having about 400 basepairs were generated to represent the different mutations. The GBLOCKS® have mutations in one or multiple oligos, where (x, x, x, x) refers to the forward primer site, m2000 first probe site, ALINITY$_m$™ HBV second probe site, and reverse primer site, respectively, and the number associated with each of these sites indicates the number of mutations introduced at that particular site (as shown in Table 10 below).

Synthetic DNA representing some of the most challenging sequences identified in public and Abbott proprietary sequence collections was interrogated with both the m2000 design and the ALINITY$_m$™ HBV design. For geneblock 29 and 36, the T denotes changing the C to T at position 12 of the main probe site. For geneblock 29, in addition to the C to T position change, two more mutations were introduced at the main probe site. The C to T change was made to minimize under-quantitation of genotype C. Geneblock 29 was not detected with the m2000 HBV probes (a WT HBV probe and a mutC probe) but was detected with the ALINITY$_m$™ HBV first and second oligonucleotide probes. The mutC probe was used in REALTIME™m2000 to overcome underquantitation in genotype C.

Figure 7A:
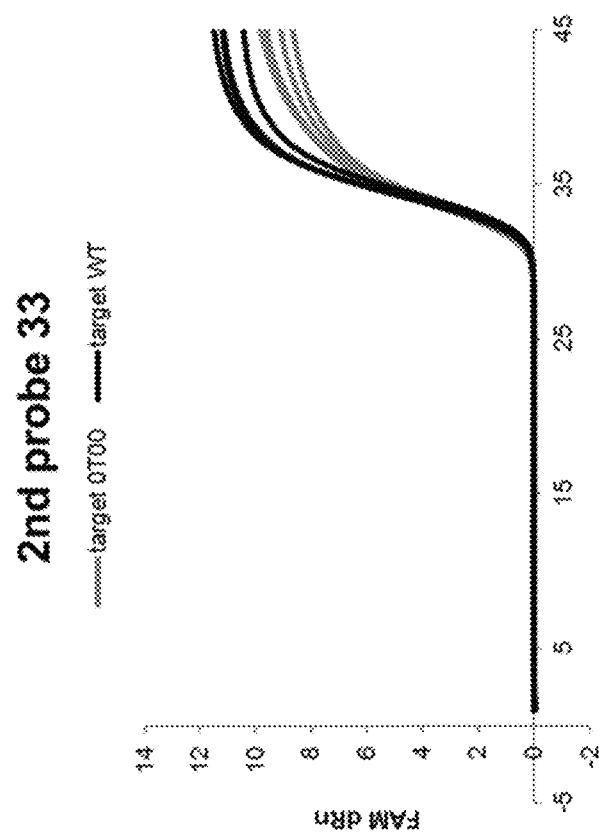
FIGS. 7A and 7B are a series of graphs that depict the results of amplification and detection of HBV genotype C (geneblock 0T00) in comparison to a wild-type (WT) HBV sequence using the Abbott REALTIME™ m2000 HBV system with a mutC probe (FIG. 7A) and the set of oligonucleotides described herein (ALINITY$_m$™ HBV system) (FIG. 7B). The x-axis corresponds to RT-PCR cycle number, and the y-axis corresponds to intensity of the FAM signal. The "secondary probe" corresponds to SEQ ID NO: 4
Figure 7B:
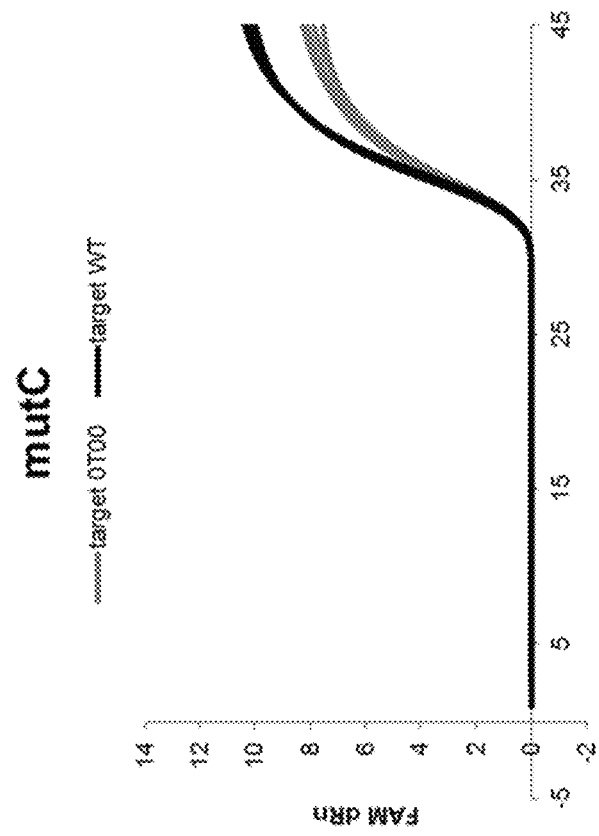

In order to demonstrate that replacing the second probe in ALINITY$_m$™ HBV with mutC probe does not cause under-quantitation of genotype C (a geneblock 0T00 in which only the C at position 12 is changed to T at the main probe site), assay performance was tested comparing the WT geneblock to this mutated synthetic DNA. The mutC probe used in the REALTIME™ m2000 HBV system exhibited a later Ct (approximately 0.8 to 1) and lower intensity than the second probe in ALINITY$_m$™ HBV for both geneblock 0T00 and WT. The second probe in ALINITY$_m$™ HBV exhibited a similar but slightly earlier Ct than mutC, indicating that ALINITY$_m$™ HBV detects genotype C1 (see FIG. 7 and Table 11), and the second probe in ALINITY$_m$™ HBV exhibited an earlier FAM Ct than mutC probe.

TABLE 11

Quantitating Genotype C

| Sample ID | Target | Average FAM Ct | dCt (X-WT) |
|---|---|---|---|
| second Probe | 0T00 | 29.97 | −0.25 |
| mutC | 0T00 | 30.97 | −0.04 |
| second Probe | WT | 30.21 | |
| mutC | WT | 31.01 | |

Figure 8:
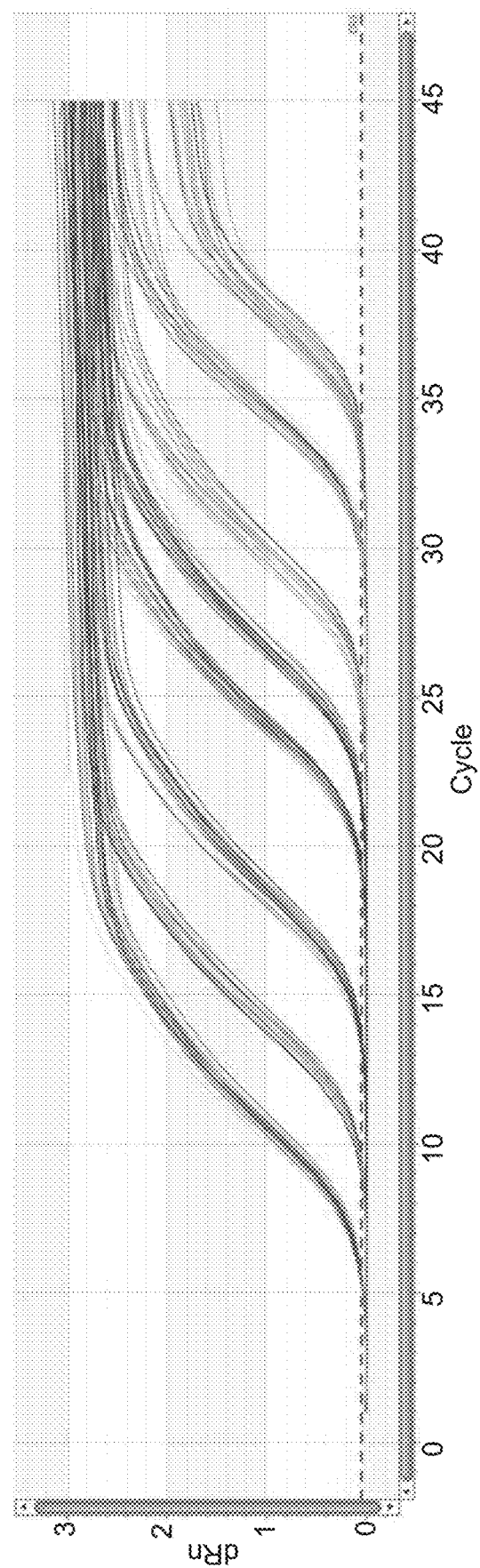
FIG. 8 is a graph that depicts PCR amplification curves across the linearity range from 1 LOG to 9 LOG IU/mL HBV containing genotype G target panels in plasma through sample extraction and using HBV amplification reagents, as described in Example 2. The results of two separate runs were combined into one graph.

Linearity was performed from 1 LOG to >8 LOG IU/mL HBV containing target panels through sample extraction and using the ALINITY$_m$™ HBV assay in two runs (see FIG. 8). Four target levels were prepared by diluting an HBV positive specimen targeting from 8.9 log IU/ml to 10 IU/ml in HBV negative normal serum.

The results of this example demonstrate that the ALINITY$_m$ HBV™ system is superior to Abbott REALTIME™ m2000 HBV detection system in detecting HBV DNA genomic sequences extracted from human plasma or serum specimens.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or

TABLE 10

Delta-CT$_{(viola-normalized)}$ Induced by Mutations in the HBV Genome

| Geneblock | 46 | 27 | 28 | 29 | 36 | 39 |
|---|---|---|---|---|---|---|
| Mutations | WT | 1, 1, 1, 0 | 0, 2, 0, 0 | 0, T/2, 0, 0 | 0, T, 2, 0 | 0, 1, 2, 0 |
| mutC | 0 | 1.56 | 1.79 | Not Detected | 1.56 | 1.37 |
| 33 | 0 | 1.11 | 0.14 | 0.48 | 2.07 | 0.68 |
| Representation: | 97.87% | 0.23% (HBV genotype G-like) | 0.03% | 0.20% | 0.20% | 0.03% |

"delta-CT" refers to the delta CT from wildtype; "Representation" indicates the frequency at which the mutations are present in public databases and Abbott collections clearly contradicted by context. The terms "comprising," "having," "including," and "containing" are to be construed as open-ended terms (i.e., meaning "including, but not limited to,") unless otherwise noted. The phrase "consisting essentially of" also is construed to be an open-ended phrase meant to include steps or materials which do not materially affect the basic and novel characteristics of a described product or method. The phrase "consisting of" is construed to be a closed phrase which excludes any element, step, or ingredient not explicitly specified in the specification or claims. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A set of oligonucleotide sequences for amplifying and detecting a nucleic acid sequence from a hepatitis B virus (HBV) capable of infecting humans in a sample, which comprises:
   (a) a forward primer oligonucleotide sequence comprising SEQ ID NO: 1;
   (b) a reverse primer oligonucleotide sequence comprising SEQ ID NO: 2;
   (c) a first probe oligonucleotide sequence comprising SEQ ID NO: 3 and a detectable label;
   (d) a second probe oligonucleotide sequence comprising SEQ ID NO: 4 and a detectable label,
   (e) an internal control forward primer oligonucleotide sequence comprising SEQ ID NO: 5,
   (f) an internal control reverse primer oligonucleotide sequence comprising SEQ ID NO: 6, and
   (g) an internal control probe oligonucleotide sequence comprising SEQ ID NO: 7 and a detectable label.

2. The set of claim 1, wherein the detectable label is a fluorophore.

3. The set of claim 1, wherein each of the probe oligonucleotides further comprises a quencher moiety.

4. A method for detecting hepatitis B virus (HBV) capable of infecting humans in a sample suspected of containing HBV, which method comprises:
   (a) contacting a sample obtained from a human with the set of oligonucleotide sequences of claim 1 and reagents for amplification and detection of nucleic acid sequences,
   (b) amplifying a first target HBV nucleic acid sequence present in the sample,
   (c) hybridizing the first and second oligonucleotide probes to the first target HBV nucleic acid sequence, and
   (d) detecting hybridization of the first and second probe oligonucleotide sequences to the first target HBV nucleic acid sequence by assessing a signal from each of the detectable labels, whereby
      (i) the presence of the signals indicates hybridization of the first and second probe oligonucleotide sequences to the first target HBV nucleic acid sequence and the presence of HBV in the sample, and
      (ii) the absence of the signals indicates the absence of HBV in the sample.

5. The method of claim 4, wherein the sample comprises serum or plasma.

6. A kit for detecting hepatitis B virus (HBV) capable of infecting humans in a sample comprising:
   (a) a forward primer oligonucleotide sequence comprising SEQ ID NO: 1;
   (b) a reverse primer oligonucleotide sequence comprising SEQ ID NO: 2;
   (c) a first probe oligonucleotide sequence comprising SEQ ID NO: 3 and a detectable label;
   (d) a second probe oligonucleotide sequence comprising SEQ ID NO: 4 and a detectable label;
   (e) an internal control forward primer oligonucleotide sequence comprising SEQ ID NO: 5;
   (f) an internal control reverse primer oligonucleotide sequence comprising SEQ ID NO: 6; and
   (g) an internal control probe oligonucleotide sequence comprising SEQ ID NO: 7 and a detectable label;
   (h) reagents for amplifying and detecting nucleic acid sequences; and
   (i) instructions for use.

7. The kit of claim 6, wherein the primers, probes, and reagents are lyophilized.

8. A composition for amplifying and detecting a hepatitis B virus (HBV) capable of infecting humans in a sample, which comprises:

(a) a forward primer oligonucleotide sequence comprising SEQ ID NO: 1;
(b) a reverse primer oligonucleotide sequence comprising SEQ ID NO: 2;
(c) a first probe oligonucleotide sequence comprising SEQ ID NO: 3 and a detectable label; and
(d) a second probe oligonucleotide sequence comprising SEQ ID NO: 4 and a detectable label;
(e) a forward primer oligonucleotide sequence comprising SEQ ID NO: 5;
(f) a reverse primer oligonucleotide sequence comprising SEQ ID NO: 6; and
(g) a probe oligonucleotide sequence comprising SEQ ID NO: 7 and a detectable label.

9. The composition of claim 8, wherein the primer oligonucleotides and probe oligonucleotides are lyophilized.

* * * * *